(12) United States Patent
Bindseil et al.

(10) Patent No.: US 7,351,262 B2
(45) Date of Patent: Apr. 1, 2008

(54) BONE IMPLANTS AND METHODS OF MAKING SAME

(75) Inventors: James J. Bindseil, Germantown, TN (US); T. Andrew Simonton, Memphis, TN (US); Cary R. Reeves, Aledo, TX (US); William F. McKay, Memphis, TN (US); Eddie F. Ray, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 10/455,771

(22) Filed: Jun. 5, 2003

(65) Prior Publication Data

US 2004/0249464 A1 Dec. 9, 2004

(51) Int. Cl.
*A61F 2/44* (2006.01)
(52) U.S. Cl. .................. 623/17.16; 623/17.11; 623/23.63; 623/23.47
(58) Field of Classification Search ............ 623/17.11, 623/17.16, 23.63, 23.47
See application file for complete search history.

(56) References Cited

U.S. PATENT DOCUMENTS

| | | | | |
|---|---|---|---|---|
| 4,326,354 A * | 4/1982 | Hagberg | ............ | 446/126 |
| 4,839,215 A * | 6/1989 | Starling et al. | ............ | 428/131 |
| 4,950,296 A | 8/1990 | McIntyre | ............ | 623/16 |
| 5,013,245 A * | 5/1991 | Benedict | ............ | 434/170 |
| 5,507,813 A | 4/1996 | Dowd et al. | ............ | 623/16 |
| 5,549,679 A | 8/1996 | Kuslich | ............ | 623/17 |
| 5,571,189 A | 11/1996 | Kuslich | ............ | 623/17 |
| 5,571,190 A | 11/1996 | Ulrich | ............ | 623/17 |
| 5,676,146 A | 10/1997 | Scarborough | ............ | 128/654 |
| 5,755,797 A * | 5/1998 | Baumgartner | ............ | 623/17.16 |
| 5,895,426 A | 4/1999 | Scarborough et al. | ........ | 623/17 |
| 5,899,939 A | 5/1999 | Boyce et al. | ............ | 623/16 |
| 6,025,538 A | 2/2000 | Yaccarino | ............ | 623/16 |
| 6,090,998 A | 7/2000 | Grooms et al. | ............ | 623/16 |
| 6,123,731 A | 9/2000 | Boyce et al. | ............ | 623/23.63 |
| 6,146,420 A | 11/2000 | McKay | ............ | 623/17 |
| 6,200,347 B1 * | 3/2001 | Anderson et al. | ........ | 623/16.11 |
| 6,270,528 B1 | 8/2001 | McKay | ............ | 623/17.11 |
| 6,294,041 B1 | 9/2001 | Boyce et al. | ............ | 156/275.5 |
| 6,315,795 B1 | 11/2001 | Scarborough et al. | ..... | 623/7.11 |
| 6,322,414 B1 * | 11/2001 | Lin | ............ | 446/122 |
| 6,371,988 B1 | 4/2002 | Pafford et al. | ............ | 623/17.11 |
| 6,379,385 B1 | 4/2002 | Kalas et al. | ............ | 623/17.11 |
| 6,387,130 B1 * | 5/2002 | Stone et al. | ............ | 623/17.16 |
| 6,409,765 B1 | 6/2002 | Bianchi et al. | ............ | 623/17.11 |
| 6,458,158 B1 | 10/2002 | Anderson et al. | ........ | 623/16.11 |
| 6,468,311 B2 | 10/2002 | Boyd et al. | ............ | 623/17.16 |
| 6,503,277 B2 | 1/2003 | Bonutti | ............ | 623/11.11 |
| 2001/0020186 A1 | 9/2001 | Boyce et al. | ............ | 623/17.16 |

(Continued)

FOREIGN PATENT DOCUMENTS

WO WO 99/29271 6/1999

(Continued)

*Primary Examiner*—Corrine McDermott
*Assistant Examiner*—Christopher Prone
(74) *Attorney, Agent, or Firm*—Woodard, Emhardt, Moriarty, McNett & Henry LLP

(57) ABSTRACT

The present invention provides an implant for use in fusing adjacent bony structures. The implant comprises a plurality of pieces of bone and a flexible mechanism including one or more flexible, elongate, biocompatible connectors interconnecting the pieces of bone.

46 Claims, 3 Drawing Sheets

U.S. PATENT DOCUMENTS

| | | | |
|---|---|---|---|
| 2001/0031254 A1* | 10/2001 | Bianchi et al. | 424/93.7 |
| 2001/0032017 A1 | 10/2001 | Alfaro et al. | 623/17.11 |
| 2001/0039456 A1 | 11/2001 | Boyer et al. | 623/23.52 |
| 2001/0039457 A1 | 11/2001 | Boyer et al. | 623/23.52 |
| 2001/0039458 A1 | 11/2001 | Boyer et al. | 623/23.63 |
| 2001/0041941 A1 | 11/2001 | Boyer et al. | 623/23.52 |
| 2001/0049560 A1 | 12/2001 | Paul et al. | 623/17.16 |
| 2001/0056302 A1 | 12/2001 | Boyer et al. | 623/17.15 |
| 2002/0029082 A1 | 3/2002 | Muhanna | 623/17.11 |
| 2002/0029084 A1 | 3/2002 | Paul et al. | 623/23.63 |
| 2002/0045944 A1 | 4/2002 | Muhanna et al. | 623/17.16 |
| 2002/0062153 A1 | 5/2002 | Paul et al. | 623/17.11 |
| 2002/0082693 A1 | 6/2002 | Ahlgren | 623/17.11 |
| 2002/0091447 A1 | 7/2002 | Shimp et al. | 623/17.16 |
| 2002/0165612 A1 | 11/2002 | Gerber et al. | 623/17.11 |
| 2003/0045934 A1 | 3/2003 | Bonutti | 623/11.11 |
| 2003/0050708 A1 | 3/2003 | Bonutti | 623/23.57 |

FOREIGN PATENT DOCUMENTS

| | | |
|---|---|---|
| WO | WO 00/30568 | 6/2000 |
| WO | WO 01/49220 | 7/2001 |
| WO | WO 01/66048 | 9/2001 |
| WO | WO 01/70136 | 9/2001 |
| WO | WO 01/78798 | 10/2001 |
| WO | WO 02/24233 | 3/2002 |
| WO | WO 02/056800 A2 | 7/2002 |
| WO | WO 02/064180 | 8/2002 |
| WO | WO 02/065957 | 8/2002 |
| WO | WO 02/098329 | 12/2002 |
| WO | WO 02/098332 | 12/2002 |

* cited by examiner

BONE IMPLANTS AND METHODS OF MAKING SAME

BACKGROUND

Implants for use in fusing adjacent bony structures facilitate fusion by maintaining the adjacent bony structures in a predetermined spaced relationship while bone grows between them. In some cases these implants are formed from body tissues. In forming an implant from body tissue, a source of tissue, such as a bone, is formed into pieces meeting the desired shape and strength requirements for a particular implant. In the case of bone, the requirements are often specified in terms of a minimum wall thickness, minimum load bearing capacity, and/or geometric size and shape. A portion of the source tissue, including pieces removed in forming implants, will fall short of the requirements to form an integral implant. Thus, it is often difficult to obtain a high yield from a particular source.

SUMMARY

The present invention provides an implant for use in fusing adjacent bony structures.

In one aspect of the invention, an implant for use in fusing adjacent bony structures comprises a plurality of pieces of bone and a flexible mechanism including one or more flexible, elongate, biocompatible connectors interconnecting the pieces of bone.

In another aspect of the invention, the implant further comprises a substrate and the interconnected bone pieces form a string of interconnected bone pieces combined with the substrate to form the implant.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DETAILED DESCRIPTION

Figure 1:
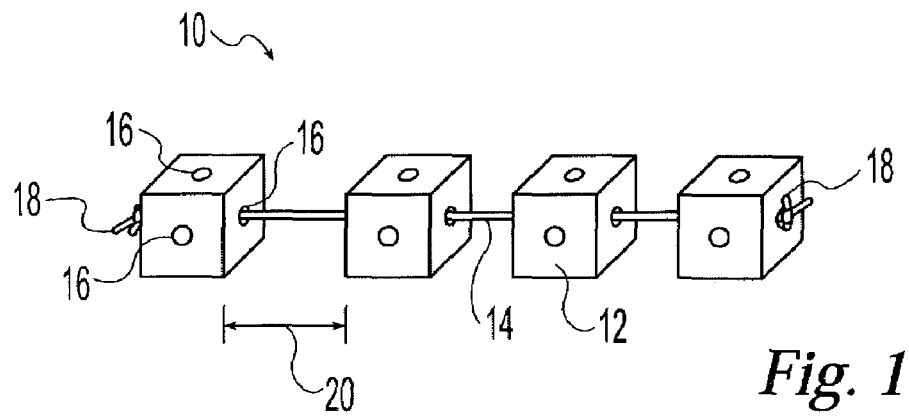
FIG. 1 is a perspective view of an illustrative embodiment of interconnected bone pieces used to make an implant according to the present invention.

Embodiments of a bone implant include a plurality of bone pieces interconnected by a flexible mechanism formed into a load bearing implant for use in fusing adjacent bony structures. The adjacent bony structures may include vertebrae, long bones, and cranial bones, among others. Bone for the implant may be obtained from any suitable bone source including the implant recipient as in an autograft, another source of the same species as in an allograft, or a source of a different species as in a xenograft. Suitable examples of musculoskeletal tissue include humerus, tibia, femur, fibula, patella, ulna, radius, rib, vertebral bodies, etc. The bone pieces may be formed by machining, planing, grinding, grating, cutting, milling, splintering, chopping, crushing, and/or other suitable means for removing bone or reducing the source bone into smaller pieces. The bone pieces may be in the form of particles, random shaped chunks, fibers, strips, sticks, rectangular prisms, cubes, spheres, cylinders and/or any other suitable shape. Each of the bone pieces may comprise a cortical bone layer. Each cortical bone piece may have a predetermined cortical layer thickness or geometry less than a predetermined minimum wall thickness or geometry associated with an integral or assembled implant formed of the donor bone. Combining a plurality of bone pieces into an implant thereby allows donor bone having less than a predetermined minimum load bearing strength or geometry to be used to form a load-bearing implant. The bone pieces may have any suitable longitudinal length, any suitable width, and any suitable height. Additionally, each of the plurality of pieces may further include a cancellous bone layer adjacent to the cortical bone layer.

One or more flexible mechanisms may interconnect the plurality of pieces or strips of bone to form a load-bearing implant. The flexible mechanism may include one or more flexible, elongate, biocompatible connectors interconnecting the pieces of bone. Examples of materials from which the connectors may be made include: pericardium, demineralized bone, fascia, cartilage, tendon, ligament, skin, collagen, elastin, reticulum, intestinal submucosa, metal, resorbable polymer, nonresorbable polymer, and/or other suitable materials.

The flexible mechanism may space the pieces of bone such that the adjacent pieces are separated by a predetermined spacing. The adjacent pieces of bone may have minimal or no spacing between them resulting in a relatively rigid interconnected implant. Alternatively, the spacing of the pieces of bone may be such as to provide a relatively flexible interconnected implant. The spacing of adjacent bone pieces may permit folding of the implant at the adjacent interconnected pieces. Rigid and flexible spacing may be combined in one implant such that the predetermined spacing may differ between a first pair of adjacent pieces of bone and a second pair of adjacent pieces of bone such that a first portion of the implant is relatively rigid and a second portion of the implant is relatively flexible. Such an implant may be folded at the second portion to provide a thicker implant folded back on itself with relatively rigid portions between the folds. Movement of the bone pieces relative to the flexible mechanism may be limited by a securing mechanism such as a knot tied in the flexible mechanism, a stopper secured to the flexible mechanism, bonding of the bone pieces to the flexible mechanism, and/or other suitable securing mechanisms. A stopper may be secured to the flexible mechanism by crimping, using an adhesive, and/or other suitable means. The flexible mechanism may attach to the exterior of the bone pieces and/or the bone pieces may each include one or more apertures through which the flexible mechanism engages the bone piece.

The interconnected bone pieces may be formed into one or more load bearing implant layers. For example, a plurality of interconnected pieces of bone may form a layer. Also, a plurality of interconnected strings, or chains, of pieces may be adjacently positioned and/or interconnected to form a layer. Additionally, a plurality of interconnected bone pieces may be formed into a layer, and multiple interconnected bone layers may be formed into an implant such as by rolling or folding a single layer to form multiple layers or by stacking multiple single layers adjacent to one another. Implants having one or more layers may have a layer axis substantially normal to the one or more layers and a load bearing axis along which load is applied to the implant from the adjacent bony structures. The implant may be oriented with its layer axis substantially perpendicular to, substantially parallel to, or at some other suitable angle to the load bearing axis.

Further, the plurality of layers may be secured together by an additional interconnection mechanism that ties together the layers. Examples of interconnection mechanisms include weaving, pinning, suturing, pressing, incorporating a binding agent, collagen cross-linking, or any other method of interconnecting the layers.

In the case of weaving, strings of interconnected pieces may be woven together in a predetermined pattern to form a woven bone layer.

If the layers are pinned, holes may be formed in the pieces and rigid pins made of bone, ceramic, metal, polymers, and/or other suitable materials may be pressed into the holes to interconnect the layers.

If the layers are sutured together, two holes may be formed through one or more of the bone pieces, one hole in each piece may be used for forming strings of interconnecting bone pieces and the second hole in one or more pieces can be used to interconnect the layers.

If a binding agent is used to interconnect the layers, it may be an adhesive binding agent, a cementitious binding agent, and/or other suitable binding agent. Examples of adhesive binding agents include fibrin glue, cyanoacrylate, epoxy, polymethylmethacrylate, gelatin based adhesives, and other suitable adhesives and combinations thereof. Examples of cementitious binding agents include settable ceramics, calcium carbonate, calcium phosphate, plaster, and other suitable materials and combinations thereof.

If the pieces are interconnected by collagen cross-linking, some of the bone pieces may be partially demineralized to expose collagen fibers which may then be crosslinked by application of heat, pressure, chemicals, and/or other suitable cross-linking means.

The interconnected bone pieces and/or layers formed from them may be combined with a substrate to form the implant. For example, a substrate having a suitable shape may be combined with a string of interconnected bone pieces by winding, weaving, coiling, packing, or otherwise positioning the string of bone pieces around and/or in the substrate. The bone pieces may be further attached to the substrate by pinning, suturing, pressing, incorporating a binding agent, collagen cross-linking, and/or any other suitable connection method as discussed relative to layer interconnection. The substrate may be in the shape of a rectangular prism, sphere, box, toroid, cylinder, pipe, "D"-shape, "C"-shape, and/or any other suitable shape. The substrate may be made of bone, resorbable polymers, nonresorbable polymers, metals, ceramics, carbon, and/or any other suitable material.

The implant may further include one or more openings through the implant to facilitate fusion of the adjacent bony structures. The one or more openings may be formed by drilling, cutting, punching, or other suitable means. The implant may further include a bone growth promoting material within the one or more layers, between the layers, and or in the one or more openings, if present. Examples of bone growth promoting material includes growth factors, osteogenic proteins, bone morphogenic proteins, including human recombinant bone morphogenic proteins, LIM mineralization proteins, bone paste, bone chips, demineralized bone, hydroxyapatite, hormones, platelet derived growth factors, bone marrow aspirate, stem cells, platelet derived growth factors, and/or other suitable bone growth promoting materials. The one or more openings may have a longitudinal axis and be oriented such that its longitudinal axis is parallel to the load bearing axis of the implant to further promote fusion between the adjacent bony structures.

Figure 2:
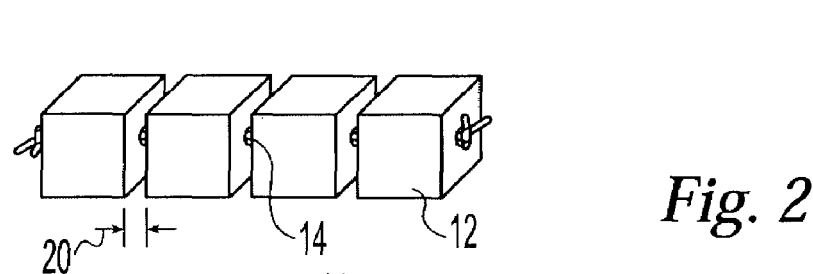
FIG. 2 is a perspective view of the interconnected bone pieces of FIG. 1 with an alternate spacing between the pieces.
Figure 3:
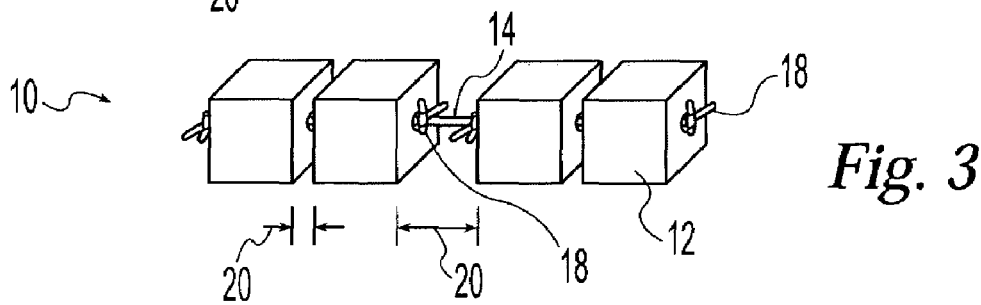
FIG. 3 is a perspective view of the interconnected bone pieces of FIG. 1 with an alternate spacing between the pieces.

Referring to FIGS. 1-3 an illustrative implant 10 includes a plurality of pieces of bone 12 interconnected by a flexible mechanism 14 to form a string, or chain, of interconnected bone pieces. The flexible mechanism may be a single connector as shown in FIG. 1 or a plurality of connectors as shown in FIG. 3. In the illustrated embodiment, the pieces of bone include holes 16 through which the flexible mechanism 14 is threaded. The bone pieces are spaced a predetermined distance 20 from one another. In FIG. 1, the predetermined distance is relatively wide resulting in a relatively flexible implant. In FIG. 2, the predetermined distance 20 is minimal resulting in a relatively rigid implant. In FIG. 3, the predetermined distance 20 varies resulting in portions of the implant that are relatively flexible and portions that are relatively rigid. The configuration of FIG. 3 facilitates folding the implant, such as folding it back on itself, at the relatively wide predetermined distance 20 to form a layered implant. A securing mechanism 18, such as a cap or knot, may be utilized to limit movement of the bone pieces 12 relative to one another and/or the flexible mechanism 14. Alternatively, the bone pieces 12 may be bonded to the flexible mechanism 14.

Figure 4:
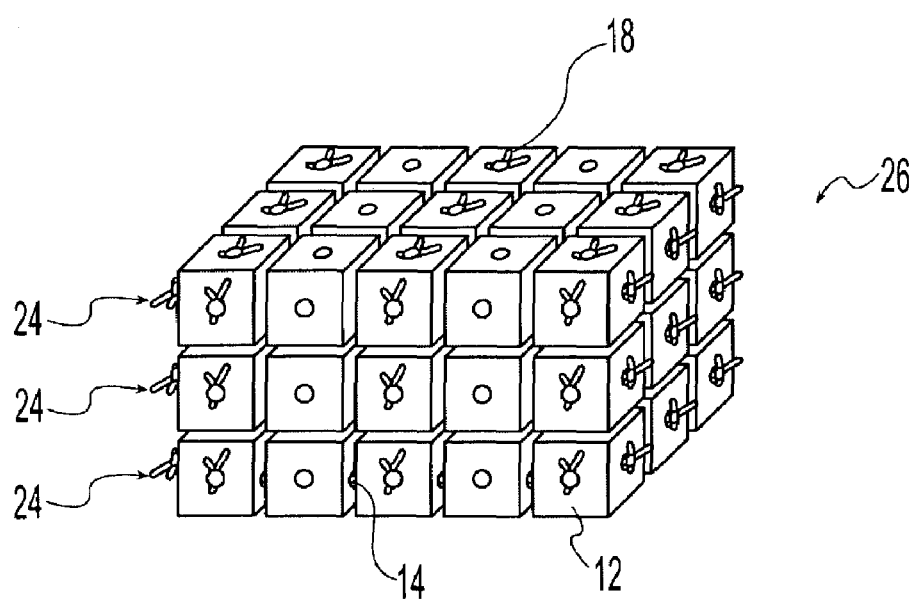
FIG. 4 is a perspective view of a multi-layered implant formed by combining interconnected bone pieces as in FIGS. 1-3.

The bone pieces may be provided with multiple holes to permit further interconnection. In FIG. 1, the bone pieces are depicted as cubes with holes oriented substantially normal to one another through the six faces of the cube. Multiple strings of bone pieces 10, like those in FIG. 1, are combined to form the layered implant 26 of FIG. 4. Strings of bone pieces 10 are positioned adjacent one another to form an implant of the desired dimensions. Additional connectors are threaded through the additional holes provided in the bone pieces to tie the strings of bone pieces 10 together into layers 24 and the final implant 26.

Figure 5:
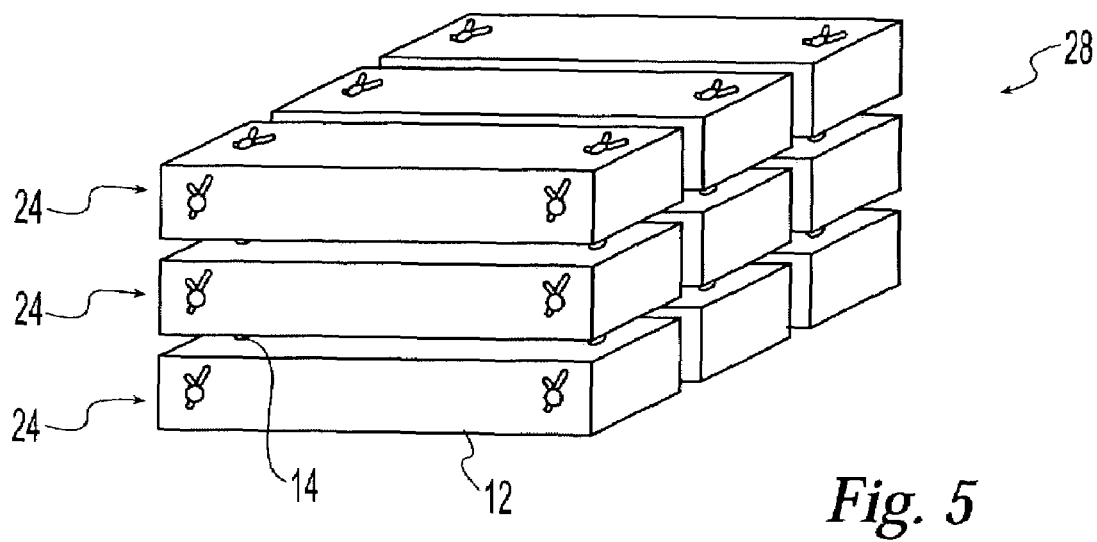
FIG. 5 is a perspective view of a multi-layered implant formed by combining interconnected bone pieces as in FIGS. 1-3, the bone pieces being more elongate.

In FIG. 5, a plurality of elongate 12 bone pieces are interconnected to form layers 24 which are stacked and tied together to form a layered implant 28.

Figure 6:
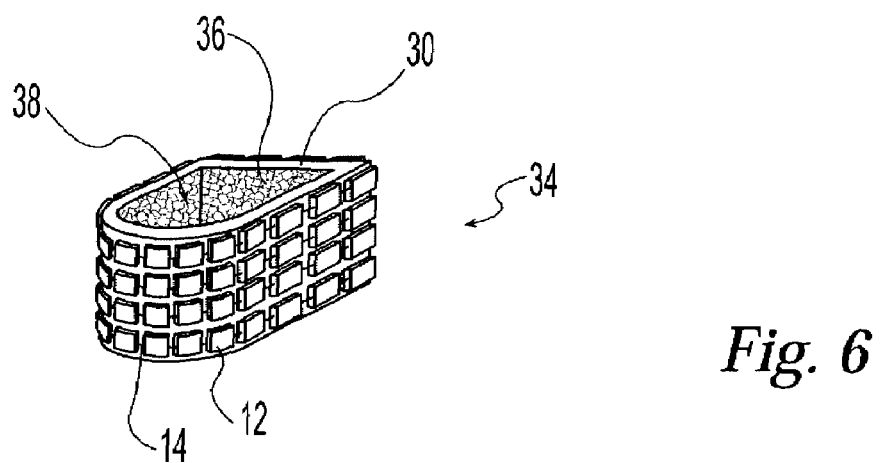
FIG. 6 is a perspective view of an implant formed by combining the interconnected bone pieces of FIG. 1 with a substrate.
Figure 7:
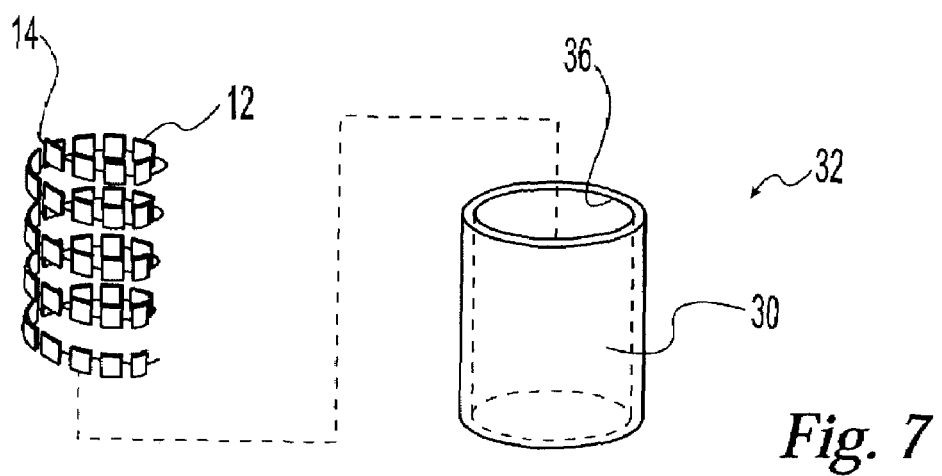
FIG. 7 is a perspective view of an implant formed by combining the interconnected bone pieces of FIG. 1 with a substrate.

Alternately, as shown in FIG. 6, one or more strings of interconnected bone pieces may be woven, wound or coiled to form the implant 34. The one or more strings may be combined with a substrate 30 to impart a predetermined shape and/or rigidity to the implant 34. The illustrative substrate is in the form of a hollow "D" shape. The interconnected pieces of bone are spirally wound around the implant to form the implant having the desired geometry and load bearing capacity. The implant further includes a hole 36 to promote fusion of the adjacent bony structures. A bone growth promoting material 38 is incorporated with the implant, such as within the hole 36, to further promote fusion. FIG. 7 illustrates an alternate configuration 32 comprising a hollow cylindrical substrate 30 with a string of interconnected bone pieces coiled and placed within the hole 36.

Figure 8:
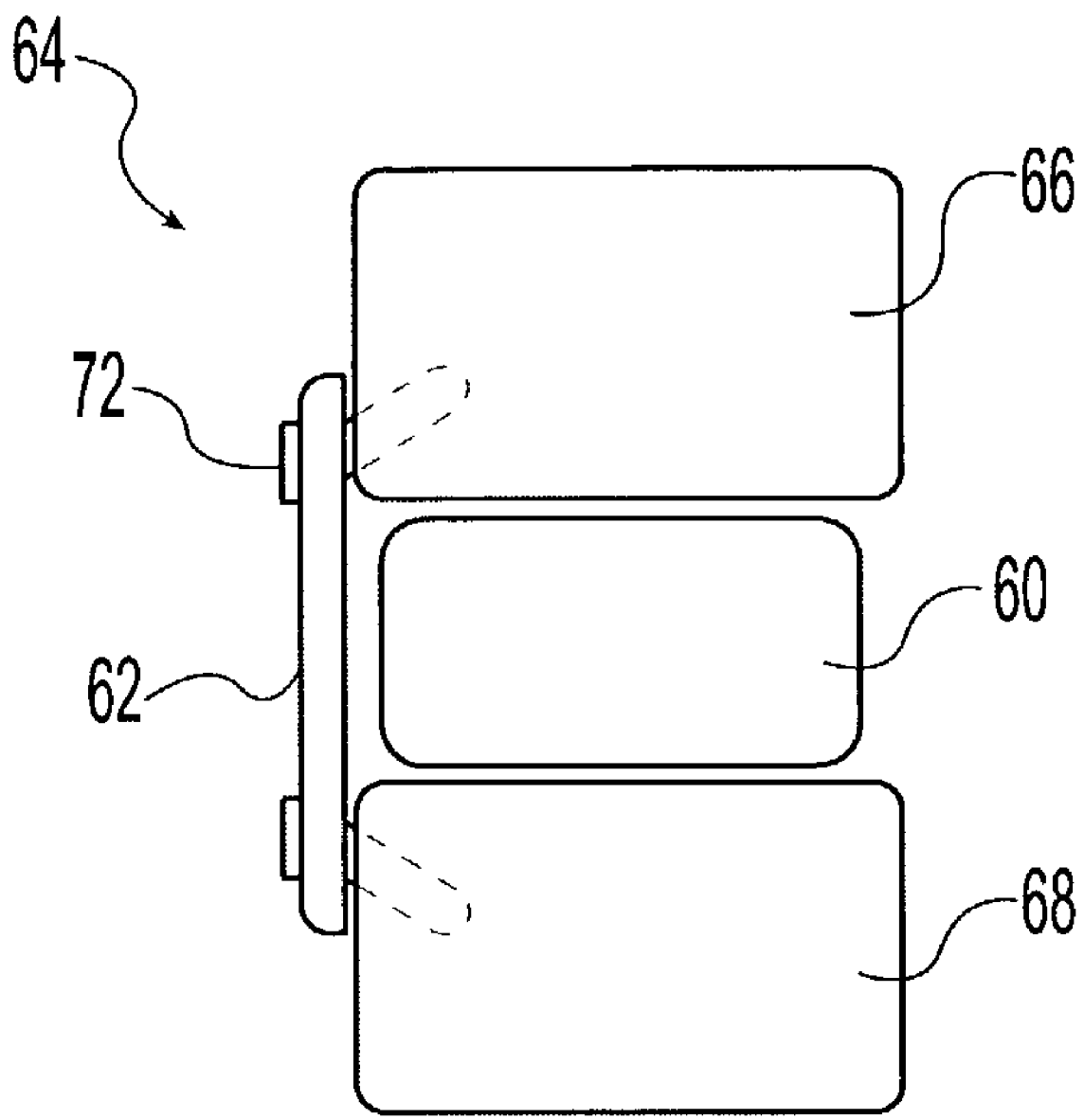
FIG. 8 is a side elevation view schematically showing an implant as in FIGS. 1-7 in combination with a supplemental fixation device mounted on a bone.

FIG. 8 schematically depicts an implant 60, such as those described above, utilized in conjunction with a fixation device 62 to form a bone fixation system 64. In such a system 64, the fusion implant 60 is positioned between adjacent bony structures 66, 68 desired to be fused together. The fixation device 62 may include one or more anchor mechanisms 72, such as screws, pins, wires, and/or other mechanisms for attaching it to the adjacent bony structures 66, 68 to limit the relative motion between them. The fixation device 62 may substantially prevent all relative motion, or it may allow a predetermined amount of motion, such as to allow the implant 60 to remain in contact with the adjacent bony structures 66, 68 during the healing and fusion processes. Suitable examples of a fixation device 62 include plates, internal or external rod systems, cable systems, cerclage systems, screws, and other suitable devices and combinations thereof.

Bone pieces comprising cortical bone may have a predetermined layer thickness and geometry, measured radially from the longitudinal axis of the donor bone, less than a predetermined minimum wall thickness and geometry. For example, the predetermined layer thickness and geometry may be in the range of less than 2 mm thick in one embodiment, less than 1.8 mm thick in another embodiment, less than 1.5 mm thick in yet another embodiment, less than 1.0 mm thick in still another embodiment, and less than 0.5 mm thick in another embodiment. Further, for example, the predetermined minimum wall thickness and geometry may relate to a minimum acceptable thickness or geometry associated with forming an integral or assembled load bearing implant. The predetermined minimum cortical geometry may vary depending on the application. For example, a minimum geometry for use in the cervical spine may be substantially less than a minimum cortical geometry for the lumbar spine. For instance, a predetermined minimum wall thickness or geometry for integral or assembled cortical wedge cervical spine implant, such as may be formed from a fibula, may be 3.0 mm in one embodiment, 2.5 mm in another embodiment, 2.0 mm in yet another embodiment, and 1.8 mm in still another embodiment. On the other hand, a minimum cortical geometry for an integral or assembled lumbar implant may be 4.5 mm in one embodiment, 4.0 mm in another embodiment, and 3.5 mm in another embodiment.

Implants formed from a plurality of bone pieces may have a compressive strength, or load bearing capability, in the range of 50N to 20,000N. For instance, embodiments may have compressive strength greater than 70N, or greater than 800N, or greater than 1000N, or greater than 1200N, or greater than 3000N, or greater than 5000N, or greater than 7000N, or greater than 10,000N, or greater than 12,000N, or greater than 15,000N, or greater than 17,000N. This compressive strength provides load-bearing capability greater than typical cancellous bone and up to that of typical cortical bone.

Although embodiments of bone implants and methods of making bone implants have been described and illustrated in detail, it is to be understood that the same is intended by way of illustration and example only and is not to be taken by way of limitation. Accordingly, variations in and modifications to the implants and methods will be apparent to those of ordinary skill in the art, and the following claims are intended to cover all such modifications and equivalents.

What is claimed is:

1. A load bearing implant for use in fusing adjacent bony structures comprising a plurality of pieces of bone and a flexible mechanism including a plurality of flexible, elongate, biocompatible connectors interconnecting the pieces of bone;

wherein said plurality of pieces of bone includes at least a first piece of bone, a second piece of bone, and a third piece of bone, wherein said first piece of bone comprises at least a first through hole extending therethrough in a first direction and a second through hole extending therethrough in a second direction wherein said second direction is transverse to said first direction, said second piece of bone comprises at least a first through hole extending therethrough, and said third piece of bone comprises at least a first through hole extending therethrough;

wherein said plurality of flexible, elongate, biocompatible connectors includes at least a first flexible, elongate, biocompatible connector extending through said first through hole of said first piece of bone and through said first through hole of said second piece of bone, and a second flexible, elongate, biocompatible connector separate from said first flexible, elongate, biocompatible connector, said second flexible, elongate, biocompatible connector extending through said second through hole of said first piece of bone and through said first through hole of said third piece of bone;

wherein said plurality of pieces of bone form a multi-layered implant in which said second piece of bone occurs laterally adjacent to said first piece of bone and said third piece of bone occurs vertically adjacent to said first piece of bone; and wherein said implant has a compressive strength greater than about 1000 Newtons.

2. The implant of claim 1 wherein the pieces of bone comprise bone substantially in the form of a rectangular prism.

3. The implant of claim 2 wherein the pieces of bone comprise bone substantially in the form of a cube.

4. The implant of claim 1 wherein the flexible mechanism extends between adjacent pieces of bone and some of the pieces of bone are folded back on other pieces of bone by folding the flexible mechanism extending between adjacent pieces of bone.

5. The implant of claim 1 wherein the individual pieces of bone comprise at least a cortical bone portion having a predetermined load-bearing capability.

6. The implant of claim 5 wherein the individual pieces of bone further comprise a cancellous bone portion.

7. The implant of claim 1 wherein said first through hole of said first piece of bone and said second through hole of said first piece of bone extend in directions that are substantially normal to one another.

8. The implant of claim 1 further including a securing mechanism to limit movement of one or more bone pieces relative to the flexible mechanism.

9. The implant of claim 8 wherein the securing mechanism comprises one or more knots tied in the flexible mechanism adjacent the pieces of bone.

10. The implant of claim 8 wherein the securing mechanism comprises one or more stoppers secured to the flexible mechanism adjacent the pieces of bone.

11. The implant of claim 10 wherein the stopper is crimped onto the flexible mechanism.

12. The implant of claim 1 wherein the pieces of bone are spaced apart a predetermined spacing between adjacent interconnected pieces.

13. The implant of claim 12 wherein there is minimal or no spacing between the pieces of bone to form a relatively rigid interconnected implant.

14. The implant of claim 12 wherein the spacing between the pieces of bone results in a relatively flexible interconnected implant.

15. The implant of claim 12 wherein the spacing between the pieces of bone permits folding the interconnected pieces back on themselves.

16. The implant of claim 12 wherein the predetermined spacing is substantially the same between consecutive pairs of interconnected pieces of bone.

17. The implant of claim 1 wherein the individual pieces of bone have a predetermined geometry outside of a predetermined standard associated with a unitary implant and the combined pieces form an assembled implant that achieves the predetermined geometry.

18. The implant of claim 1 wherein the flexible mechanism includes a plurality of flexible, elongate, biocompatible connectors comprising at least one material selected from the group consisting of pericardium, demineralized bone, fascia, cartilage, tendon, ligament, skin, collagen, elastin, reticulum, intestinal submucosa, metal, resorbable polymer, and nonresorbable polymer.

19. The implant of claim 1 wherein the interconnected bone pieces are formed into one or more load bearing implant layers.

20. The implant of claim 19 wherein the one or more layers are formed by a plurality of adjacently positioned strings of interconnected bone pieces, the adjacently positioned strings being interconnected with one another.

21. The implant of claim 20 further comprising an additional flexible mechanism interconnecting the adjacently positioned strings.

22. The implant of claim 20 wherein each piece of bone includes at least first and second through holes oriented substantially normally to one another, the pieces of bone in a string of interconnected bone being connected by a flexible connector threaded through the first through holes and the adjacently positioned strings of interconnected bone pieces being connected by a flexible connector threaded through the second through holes.

23. The implant of claim 19 wherein the one or more layers comprise a single string of interconnected bone pieces folded back on itself one or more times.

24. The implant of claim 19 further comprising a plurality of layers overlying one another along a layer axis substantially normal to the layers and a load bearing axis along which load is applied to the implant from the adjacent bony structures, the layer axis being substantially perpendicular to the load bearing axis.

25. The implant of claim 19 further comprising a plurality of layers overlying one another along a layer axis substantially normal to the layers and a load bearing axis along which load is applied to the implant from the adjacent bony structures, the layer axis being substantially parallel to the load bearing axis.

26. The implant of claim 1 further comprising a substrate and wherein the interconnected bone pieces form a string of interconnected bone pieces, the string of interconnected bone pieces being combined with the substrate to form the implant.

27. The implant of claim 26 wherein the string of interconnected bone pieces is wound around the substrate.

28. The implant of claim 26 wherein the string of interconnected bone pieces is woven around the substrate.

29. The implant of claim 26 wherein substrate further comprises an interior portion and the string of interconnected bone pieces is placed within the interior portion.

30. The implant of claim 29 wherein the string of interconnected bone pieces is coiled within the interior portion.

31. The implant of claim 29 wherein the string of interconnected bone pieces is packed within the interior portion.

32. The implant of claim 26 wherein the string of interconnected bone pieces is attached to the substrate by at least one of the attachment mechanisms selected from the list consisting of pinning, suturing, pressing, incorporating a binding agent, and collagen cross-linking.

33. The implant of claim 26 wherein the substrate comprises at least one shape selected from the group consisting of box, toroid, cylinder, pipe, sphere, "D"-shape, and "C"-shape.

34. The implant of claim 26 wherein the substrate comprises at least one material selected from the group consisting of bone, resorbable polymers, nonresorbable polymers, metal, ceramics, and carbon.

35. The implant of claim 26 wherein the substrate further includes at least one through hole to facilitate fusion of the adjacent bony structures.

36. The implant of claim 35 further comprising a load bearing axis along which load is applied to the implant from the adjacent bony structures, the at least one through hole having a longitudinal axis parallel to the load bearing axis.

37. The implant of claim 35 further comprising at least one bone growth promoting material within the at least one through hole.

38. The implant of claim 37 wherein the bone growth promoting material comprises at least one material selected from the group comprising bone derived growth factors, osteogenic proteins, human recombinant bone morphogenic proteins, LIM mineralization proteins, bone paste, bone chips, demineralized bone, hydroxyappatite, hormones, and platelet derived growth factor.

39. The implant of claim 1 further including an opening to facilitate fusion of the adjacent bony structures.

40. The implant of claim 39 further comprising at least one bone growth promoting material within the at least one opening.

41. The implant of claim 40 wherein the bone growth promoting material comprises at least one material selected from the group comprising bone derived growth factors, osteogenic proteins, human recombinant bone morphogenic proteins, LIM mineralization proteins, bone paste, bone chips, demineralized bone, hydroxyappatite, hormones, and platelet derived growth factor.

42. An implant for use in fusing adjacent bony structures comprising a plurality of pieces of bone and a flexible mechanism including a plurality of flexible, elongate, biocompatible connectors interconnecting the pieces of bone;

wherein said plurality of pieces of bone includes at least a first piece of bone, a second piece of bone, and a third piece of bone, wherein said first piece of bone comprises at least a first through hole extending therethrough in a first direction and a second through hole extending therethrough in a second direction wherein said second direction is transverse to said first direction, said second piece of bone comprises at least a first through hole extending therethrough, and said third piece of bone comprises at least a first through hole extending therethrough; and wherein said plurality of flexible, elongate, biocompatible connectors includes at least a first flexible, elongate, biocompatible connector extending through said first through hole of said first piece of bone and through said first through hole of said second piece of bone, and a second flexible, elongate, biocompatible connector separate from said first flexible, elongate, biocompatible connector, said second flexible, elongate, biocompatible connector extending through said second through hole of said first piece of bone and through said first through hole of said third piece of bone;

wherein the pieces of bone are spaced apart a predetermined spacing between adjacent interconnected pieces; and wherein the predetermined spacing differs between a first pair of adjacent pieces of bone and a second pair of adjacent pieces of bone such that a first portion of the implant is relatively rigid and a second portion of the implant is relatively flexible.

43. The implant of claim 42 wherein the implant is folded at the second pair of adjacent pieces of bone.

44. The implant of claim 1 wherein the individual pieces of bone have less than a predetermined minimum load bearing capacity and the interconnected pieces of bone form an implant that achieves a predetermined load bearing capacity greater than the predetermined minimum load bearing capacity.

45. An implant for use in fusing adjacent bony structures comprising a plurality of pieces of bone and a flexible mechanism including a plurality of flexible, elongate, biocompatible connectors interconnecting the pieces of bone;

wherein said plurality of pieces of bone includes at least a first piece of bone, a second piece of bone, and a third piece of bone, wherein said first piece of bone comprises at least a first through hole extending therethrough in a first direction and a second through hole extending therethrough in a second direction wherein said second direction is transverse to said first direction, said second piece of bone comprises at least a first through hole extending therethrough, and said third piece of bone comprises at least a first through hole extending therethrough; and wherein said plurality of flexible, elongate, biocompatible connectors includes at least a first flexible, elongate, biocompatible connector extending through said first through hole of said first piece of bone and through said first through hole of said second piece of bone, and a second flexible, elongate, biocompatible connector separate from said first flexible, elongate, biocompatible connector, said second flexible, elongate, biocompatible connector extending through said second through hole of said first piece of bone and through said first through hole of said third piece of bone;

wherein the interconnected bone pieces are formed into one or more load bearing implant layers; and wherein the one or more layers comprise a string of interconnected bone pieces formed into a wound spiral construct.

46. An implant for use in fusing adjacent bony structures comprising a plurality of pieces of bone and a flexible mechanism including a plurality of flexible, elongate, biocompatible connectors interconnecting the nieces of bone;

wherein said plurality of pieces of bone includes at least a first piece of bone, a second piece of bone, and a third piece of bone, wherein said first piece of bone comprises at least a first through hole extending therethrough in a first direction and a second through hole extending therethrough in a second direction wherein said second direction is transverse to said first direction, said second piece of bone comprises at least a first through hole extending therethrough, and said third piece of bone comprises at least a first through hole extending therethrough; and wherein said plurality of flexible, elongate, biocompatible connectors includes at least a first flexible, elongate, biocompatible connector extending through said first through hole of said first piece of bone and through said first through hole of said second piece of bone, and a second flexible, elongate, biocompatible connector separate from said first flexible, elongate, biocompatible connector, said second flexible, elongate, biocompatible connector extending through said second through hole of said first piece of bone and through said first through hole of said third piece of bone;

said implant further comprising a substrate and wherein the interconnected bone pieces form a string of interconnected bone pieces, the string of interconnected bone pieces being combined with the substrate to form the implant; and wherein the string of interconnected bone pieces is wound around the substrate in a spiral pattern.

* * * * *